US011457906B2

(12) United States Patent
Klausman

(10) Patent No.: US 11,457,906 B2
(45) Date of Patent: Oct. 4, 2022

(54) TISSUE RETRACTOR

(71) Applicant: Astura Medical Inc., Carlsbad, CA (US)

(72) Inventor: Keith Klausman, Carlsbad, CA (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/033,630

(22) Filed: Sep. 25, 2020

(65) Prior Publication Data

US 2021/0085308 A1 Mar. 25, 2021

Related U.S. Application Data

(60) Provisional application No. 62/905,387, filed on Sep. 25, 2019.

(51) Int. Cl.
*A61B 17/02* (2006.01)
*A61B 17/00* (2006.01)

(52) U.S. Cl.
CPC ........... *A61B 17/0206* (2013.01); *A61B 2017/00407* (2013.01)

(58) Field of Classification Search
CPC ... A61B 17/02; A61B 17/0206; A61B 17/025; A61B 17/0256
See application file for complete search history.

(56) References Cited

U.S. PATENT DOCUMENTS

| | | | | |
|---|---|---|---|---|
| 5,383,623 A | * | 1/1995 | Hiruta | B60R 22/4628 242/374 |
| 8,727,975 B1 | * | 5/2014 | Pfabe | A61B 17/0293 600/231 |
| 2007/0137440 A1 | * | 6/2007 | Hwang | B25B 13/06 81/59.1 |
| 2011/0224496 A1 | * | 9/2011 | Weiman | A61B 17/0206 600/219 |
| 2012/0245431 A1 | * | 9/2012 | Baudouin | A61B 17/0218 600/213 |
| 2015/0230787 A1 | * | 8/2015 | Friedrich | A61B 1/32 600/213 |
| 2019/0269469 A1 | * | 9/2019 | Bush, Jr. | A61B 34/20 |

OTHER PUBLICATIONS

International Preliminary Reporton Patentability in PCT Application No. PCT/US2020/052939 dated Dec. 17, 2020.

* cited by examiner

*Primary Examiner* — Ellen C Hammond
(74) *Attorney, Agent, or Firm* — Michael R. Shevlin

(57) ABSTRACT

A tissue retractor having a central body, a posterior housing slidably coupled to the central body via a first two way overrunning clutch, a posterior arm slidably coupled to the posterior housing via a second two way overrunning clutch, a right arm rotatably coupled to the central body via a hinge pin and third two way overrunning clutch and a left arm rotatably coupled to the central body via a hinge pin and fourth two way overrunning clutch.

20 Claims, 6 Drawing Sheets

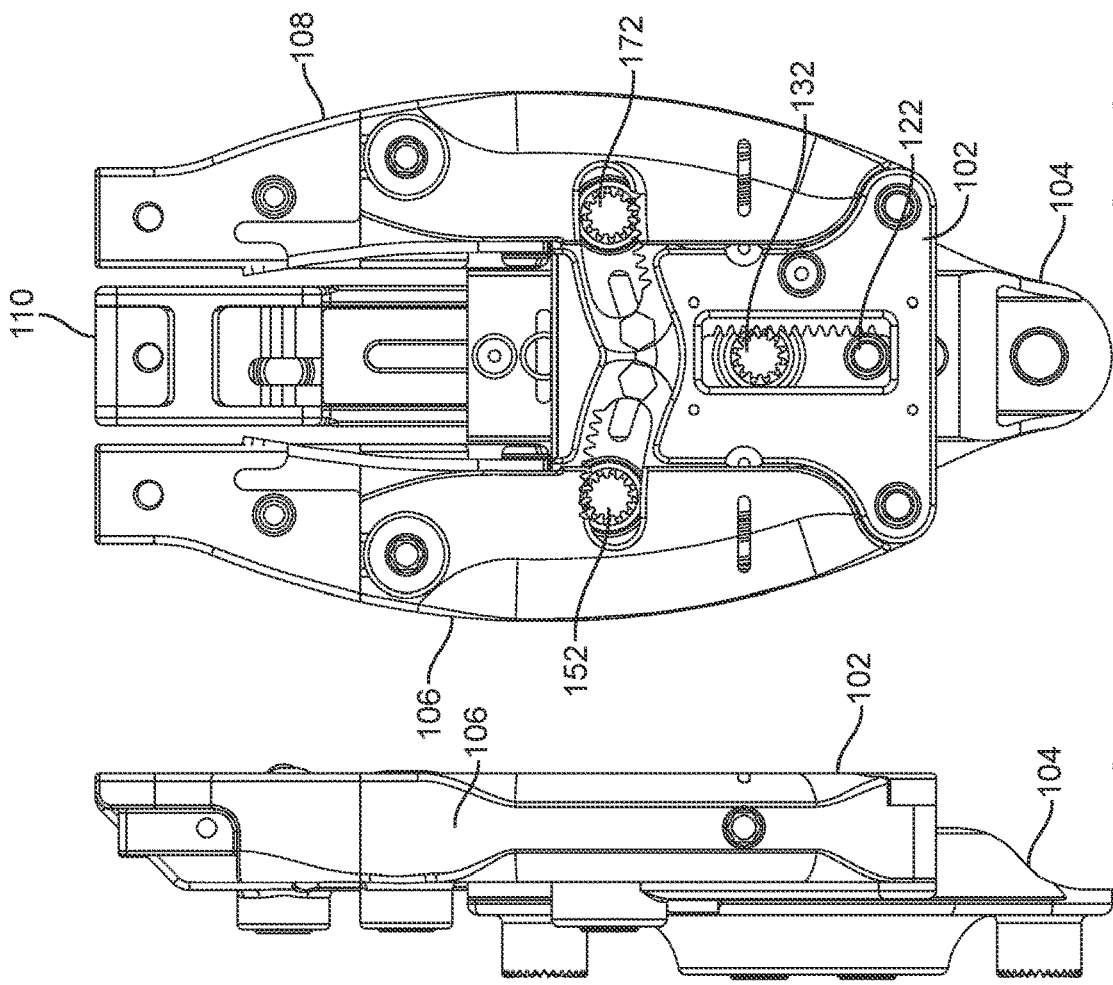

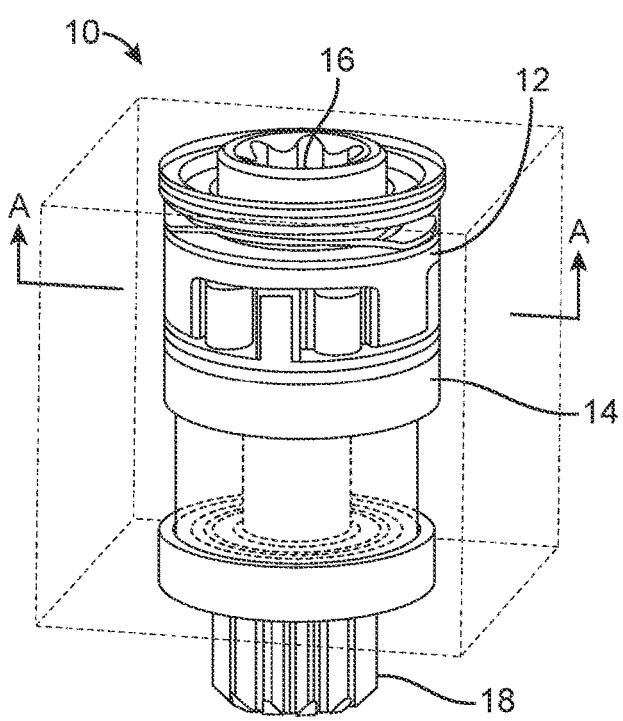
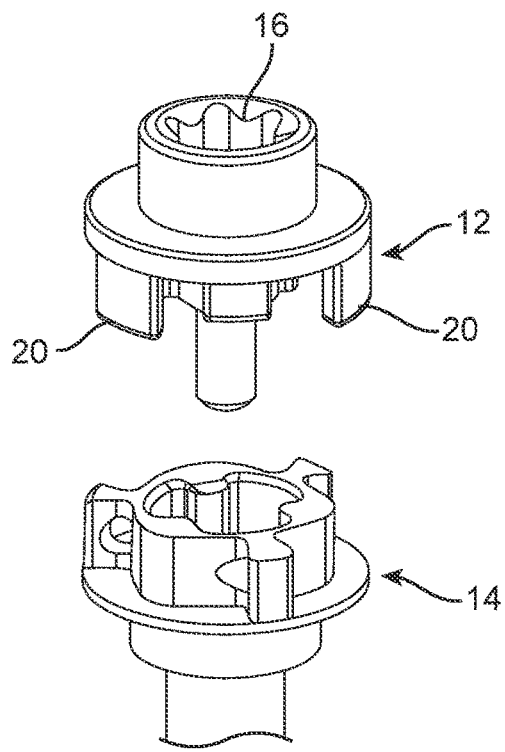
FIG. 2A
FIG. 2B
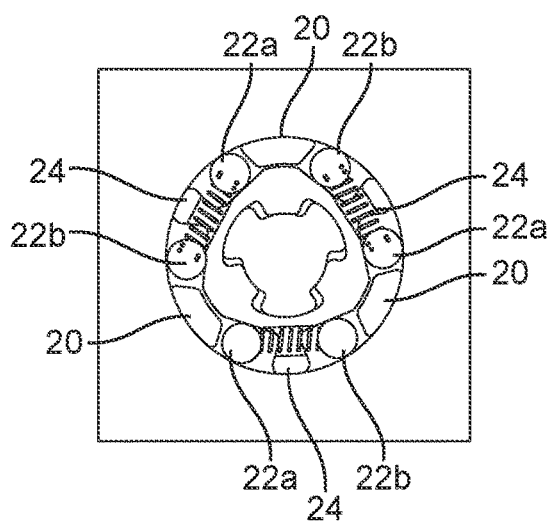
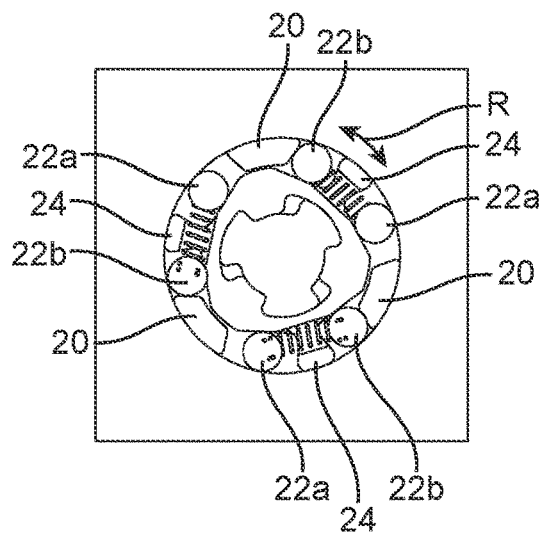
FIG. 3A
FIG. 3B

TISSUE RETRACTOR

CROSS-REFERENCE TO RELATED APPLICATIONS

This application claims the benefit of U.S. Provisional Application No. 62/905,387 filed Sep. 25, 2019, which is incorporated herein by reference.

FIELD

The present invention relates generally to the field of surgery, and more specifically, to a tissue retractor for use in Spinal Fusion Surgery.

BACKGROUND

Many types of surgeries require exposure and access through the skin to internal parts of the body ("surgical area"). The opening of the surgical area must be of sufficient size to allow the surgeon ample access for carrying out procedures The opening should also remain open during the surgery and allow the surgeon to perform the desired procedure.

Tissue retractors are typically used to perform this. The tissue retractors are typically mechanized devices designed to generate a pathway through tissue for surgical access. The mechanisms used to produce a pathway tend to rely on secondary mechanisms to maintain the pathway i.e. a ratchet. To close the pathway, the secondary mechanism typically requires a secondary action and or tool to release. These different actions and or tools are time consuming and cumbersome when the surgical procedure is time sensitive.

Prior solutions also require multiple tools across multiple limited adjustment mechanisms that require input torque to operate.

Accordingly, there remains a need for instruments and methods that provide solutions to the problems of current systems. The present invention is directed toward meeting these needs.

SUMMARY

While prior solutions require multiple tools across multiple limited adjustment mechanisms that require input torque to operate, the present invention only requires one tool utilizing one mechanism to drive the assembly in a clockwise or counterclockwise direction with zero backlash and is infinitely adjustable with no additional input torque required.

The present invention is directed to a tissue retractor having a central body, a posterior housing slidably coupled to the central body via a first two way overrunning clutch, a posterior arm slidably coupled to the posterior housing via a second two way overrunning clutch, a right arm rotatably coupled to the central body via a hinge pin and third two way overrunning clutch and a left arm rotatably coupled to the central body via a hinge pin and fourth two way overrunning clutch.

BRIEF DESCRIPTION OF THE DRAWINGS

FIGS. 1A, 1B, 1C show front, side and rear views of one embodiment of a tissue retractor.

FIGS. 2A and 2B show one embodiment of a two way overrunning clutch.

FIGS. 3A and 3B are sectional views at A-A of the clutch of FIG. 2A.

DETAILED DESCRIPTION

Figure 4:
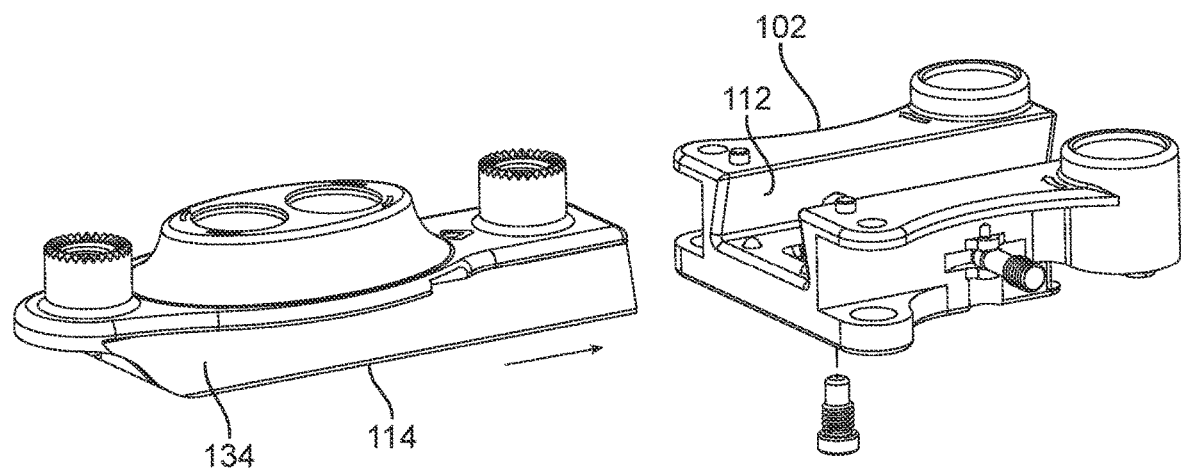
FIG. 4 shows the assembly of the central body and posterior housing.

The present invention is directed to systems, methods, and devices applicable to spinal surgery. More specifically, the present invention is directed to a tissue retractor having a two way overrunning clutch ratchet mechanism to move the components for use by medical personnel (i.e., doctor) in spinal and other surgical procedures.

FIGS. 1A, 1B, 1C show front, side and rear views of one embodiment of a tissue retractor 100. The tissue retraction includes a central body 102, a posterior housing 104, a right arm 106, a left arm 108 and a posterior arm 110.

The posterior housing 104 is slidably coupled to the central body 102 and configured to extend/retract in relation to each other via a first two way overrunning clutch 120. The posterior arm 110 is slidably coupled to the posterior housing 104 and configured to extend/retract in relation to each other via a second two way overrunning clutch 130 The right arm 106 is rotatably coupled to the central body 102 at a proximal end, and a distal end is configured to rotate in relation to each other via a third two way overrunning clutch 150. The left arm 108 is rotatably coupled to the central body 102 at a proximal end and the distal end configured to rotate in relation to each other via a third two way overrunning clutch 170.

FIGS. 2A and 2B show one embodiment of a two way overrunning clutch 10 ("clutch") that is a zero backlash anti rotational and infinitely adjustable mechanism capable of operating in a clockwise and counter-clockwise direction. The clutch includes top and bottom drive components 12, 14 having internal springs and rollers. The top drive component 12 includes a socket 16 for a tool to operate the clutch 10. The bottom drive component 12 includes a clutch gear 18 to interface with clutch gear teeth on the central body 102, posterior housing 104, right arm 106, left arm 108 and posterior arm 110.

FIGS. 3A and 3B are sectional views at A-A of the clutch 10. The top drive component 12 includes legs 20 which are positioned between each pair of opposing leading edge rollers 22a and trailing edge rollers 22b separated by springs 24. When the top drive component 12 is rotated R (input torque) in either direction, the legs 20 disengage the leading wedged rollers 22a while simultaneously engaging with the bottom drive component 14 to rotate freely in that direction. The opposing trailing wedged roller 22b maintains its position by way of the spring 24 and does not limit rotation in the opposing direction based on the wedge direction.

Once the input torque of the driver stops, the opposing trailing roller 22b limits any reverse torque (zero backlash).

FIG. 4 shows the assembly of the central body 102 and posterior housing 104. The central body 102 includes a slot 112 sized to slidable receive the lower portion 114 of the posterior housing 104.

Figure 5:
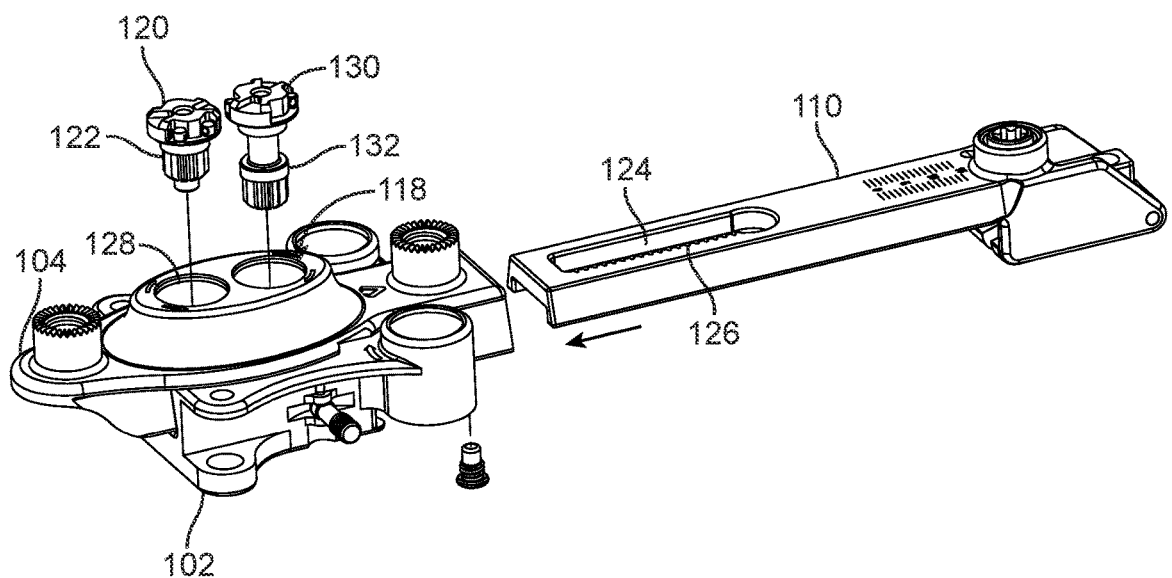
FIG. 5 shows the assembly of the central body/posterior housing assembly and the posterior arm.

FIG. 5 shows the assembly of the central body 102/posterior housing 104 assembly and the posterior arm 110. The lower portion of the posterior housing 104 includes a slot 116 that is configured to slidably receive the posterior arm 110.

The posterior housing 104 includes a first opening 128 sized to receive a first two way overrunning clutch ("clutch") 130 having a first clutch gear 132. The first clutch gear 132 is configured to fit in a slot 134 on the central body 102 and mate with teeth 136 along one side of the slot 134 so the rotation of the first clutch 130 will rotate the first clutch gear 132/teeth 136 to extend or retract the posterior housing 104 in relation to the central body 102.

The posterior housing 104 includes a second opening 118 sized to receive a second clutch 120 having a second clutch gear 122. The second clutch gear 122 is configured to fit in a slot 124 on the posterior arm 110 and mate with teeth 126 along one side of the slot 122 so the rotation of the second clutch 120 will rotate the second clutch gear 122/teeth 126 to extend or retract the posterior arm 110 in relation to the posterior housing 104.

Figure 6:
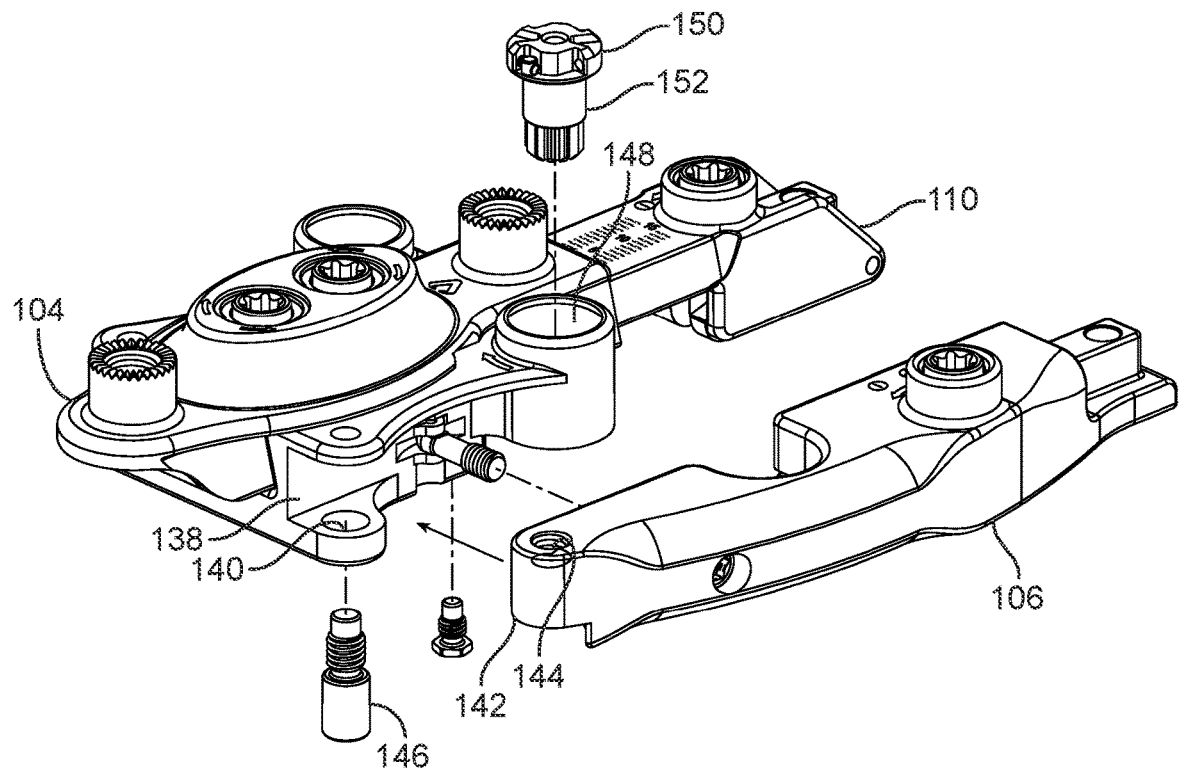
FIG. 6 shows the assembly of the central body/posterior housing assembly with the right arm.

FIG. 6 shows the assembly of the central body 102/posterior housing 104 assembly with the right arm 106. The central body 102 includes a slot 138 with pin hole 140. The slot 138 is sized to fit a proximal portion 142 of the right arm having a hole 144. After insertion of the proximal portion 142 into the slot 138, a rotation pin 146 is inserted through pin hole 140 and hole 144 so that the right arm 106 may rotate in relation to the central body 102.

The central body 102 includes a third opening 148 that is sized to receive a third clutch 150 having a third clutch gear 152. The third clutch gear 152 is configured to fit in a slot 154 in a right rotation arm 156 of the right arm 106 and mate with slot teeth 158 along one side of the slot 154 so the rotation of the clutch 150 will rotate the third clutch gear 152/teeth 158 to extend or retract right arm 106 in relation to the central body 102.

Figure 7:
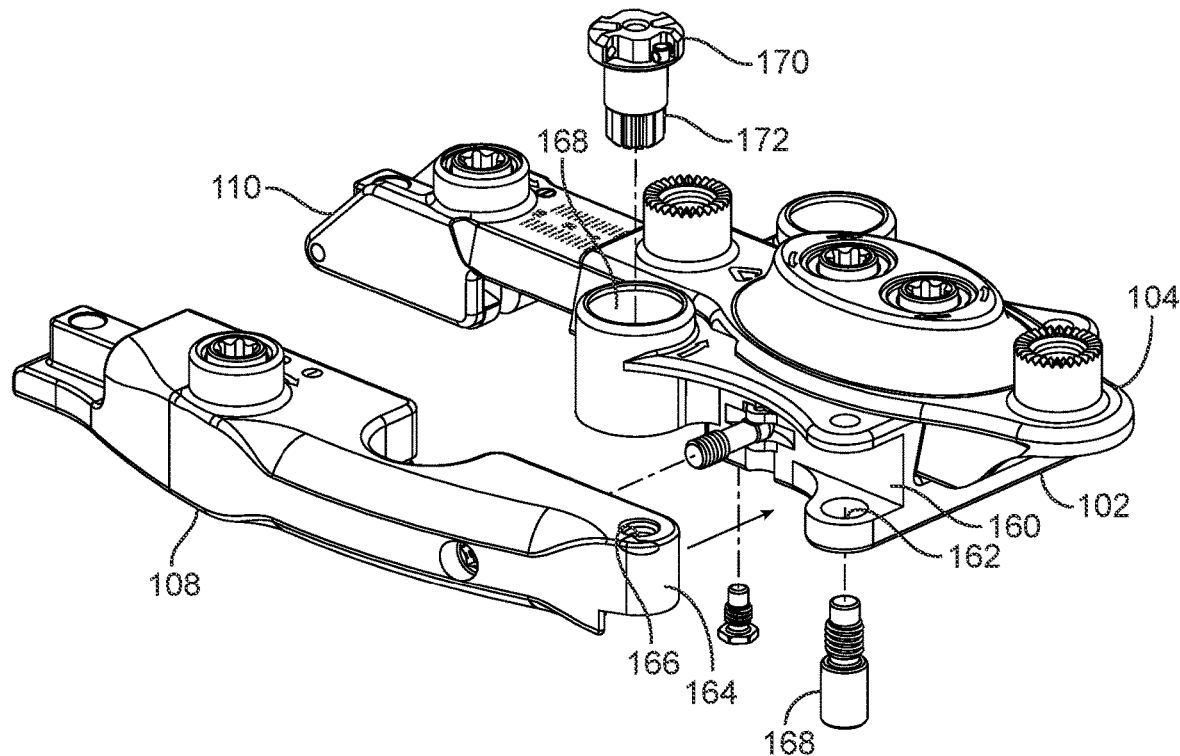
FIG. 7 shows the assembly of the central body/posterior housing assembly with the left arm.

FIG. 7 shows the assembly of the central body 102/posterior housing 104 assembly with the left arm 108. The central body 102 includes a slot 160 with pin hole 162. The slot 160 is sized to fit a proximal portion 164 of the left arm having a hole 166. After insertion of the proximal portion 164 into the slot 160, a rotation pin 168 is inserted through pin hole 162 and hole 166 so that the left arm 108 may rotate in relation to the central body 102.

The central body 102 includes a fourth opening 168 that is sized to receive a fourth clutch 170 having a clutch gear 172. The clutch gear 172 is configured to fit in a slot 174 in a left rotation arm 176 of the left arm 18 and mate with slot teeth 178 along one side of the slot 174 so the rotation of the clutch 170 will rotate the clutch gear 172/teeth 178 to extend or retract left arm 108 in relation to the central body 102.

Figure 8:
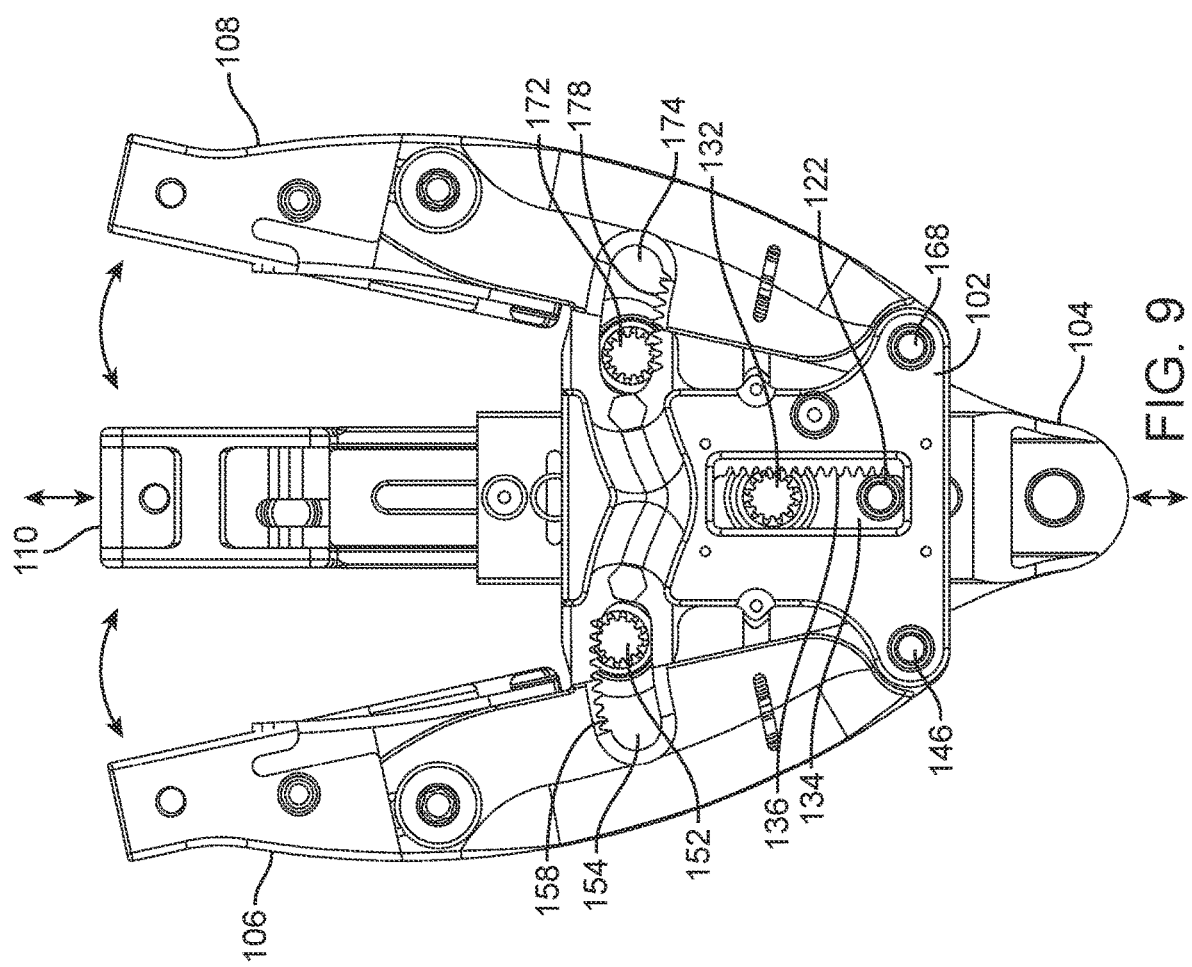
FIG. 8 is a rear view showing the components assembled together.

FIG. 8 is a rear view showing the components assembled together including the central body 102, posterior housing 104, right arm 106, left arm 108 and posterior arm 110. Rotating the two way overrunning clutches 120, 130, 150 and 170 rotates the clutch gears 122, 132, 152 and 172 moving the components. Clutch gear 122 is positioned in the slot 124 on the posterior arm 110 mating with teeth 126, clutch gear 132 is positioned in slot 134 on the central body 102 mating with teeth 136, clutch gear 152 is positioned in the slot 154 on the right arm 106 mating with teeth 158 and clutch gear 172 is positioned in slot 174 on the left arm 108 mating with teeth 178. To extend or retract the posterior housing 104 in relation to the central body 102, the first two way overrunning clutch 130 is rotated, which rotates clutch gear 132 against the teeth 136 to extend or retract the posterior housing 104. To extend or retract the posterior arm 110 in relation to the posterior housing 104, the second two way overrunning clutch 120 is rotated, which rotates clutch gear 122 against the teeth 126 to extend or retract the posterior arm 110. To rotate the right arm 106 in relation to the central body 102, the third two way overrunning clutch 150 is rotated, which rotates clutch gear 132 against the teeth 186 to rotate the right arm 106. To rotate the left arm 108 in relation to the central body 102, the fourth two way overrunning clutch 170 is rotated, which rotates clutch gear 172 against the teeth 178 to rotate the left arm 108.

Figure 9:
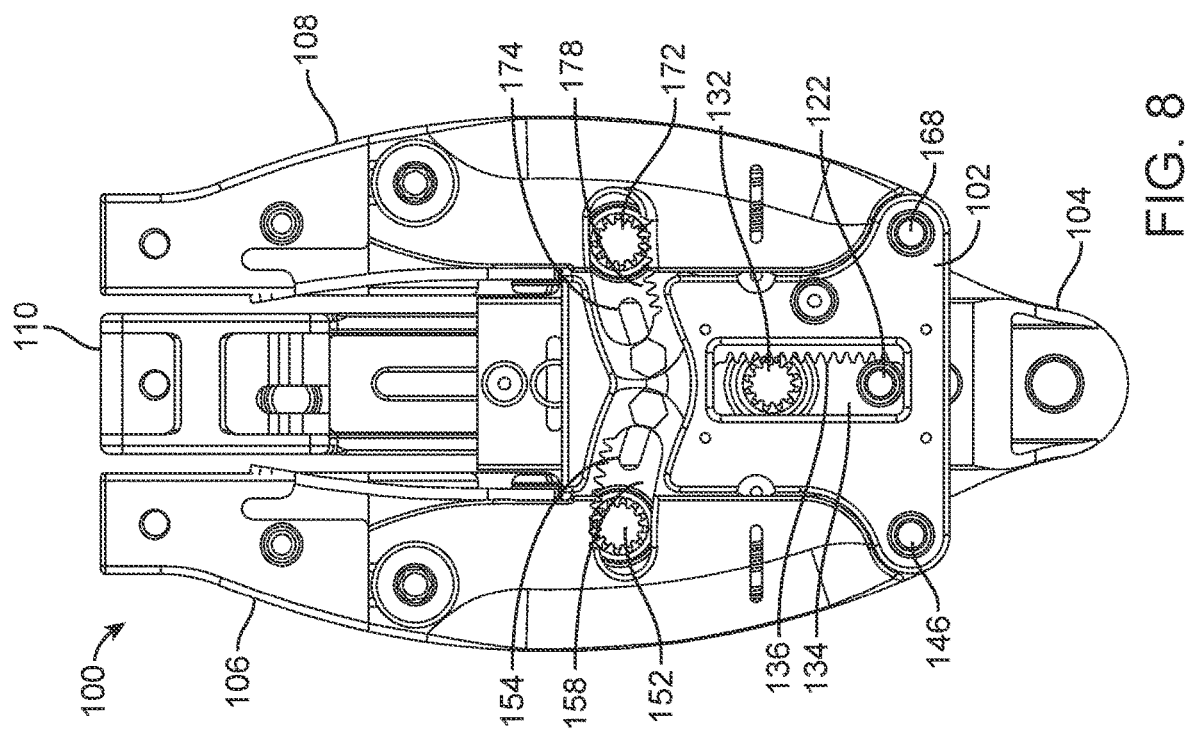
FIG. 9 is a rear view showing the right arm and left arm rotated outwardly at the distal ends.

FIG. 9 is a rear view showing the right arm 106 and left arm 108 rotated outwardly at the distal ends.

Figure 10:
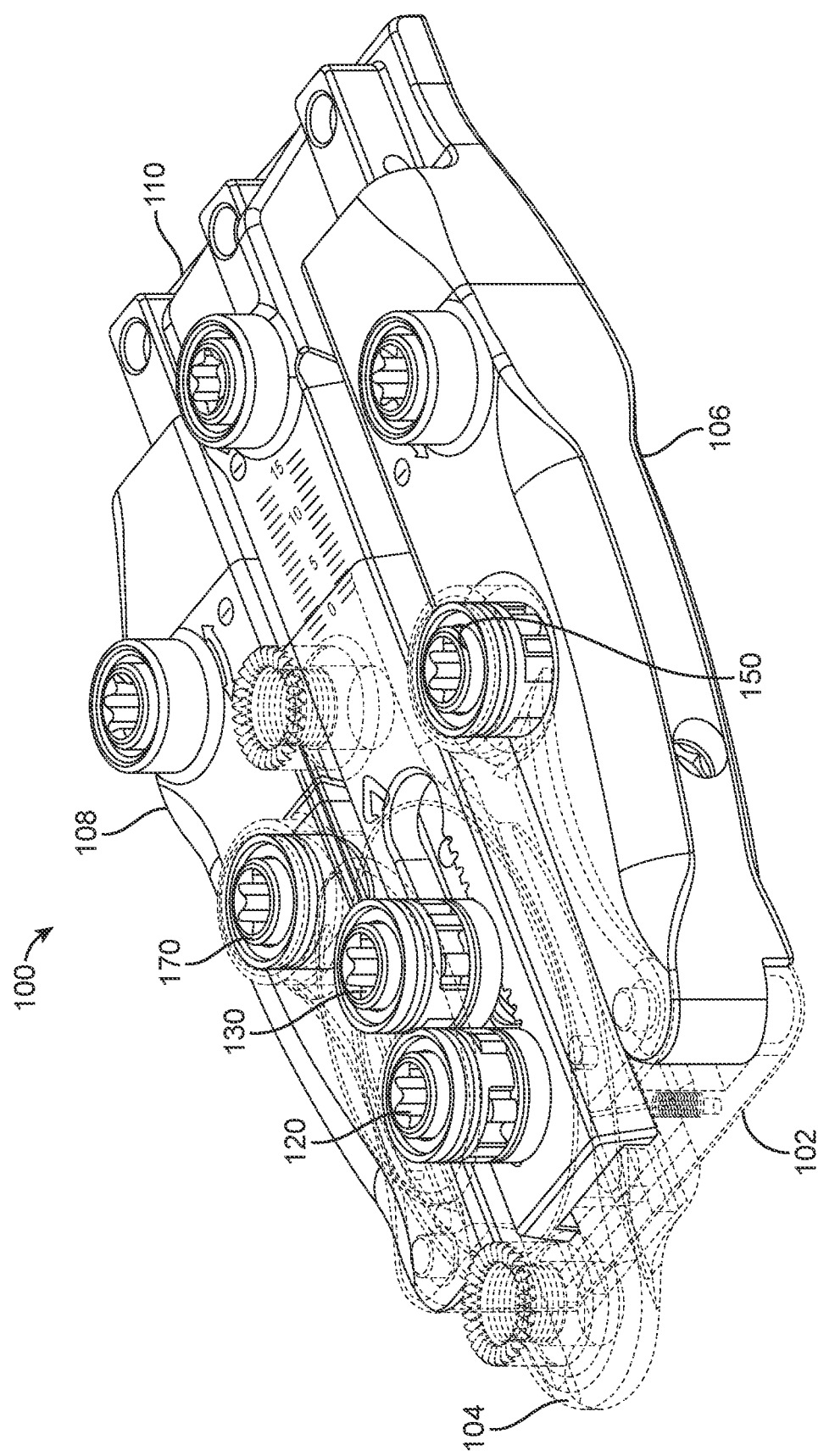
FIG. 10 is a prospective view of the tissue retractor 100.

FIG. 10 is a prospective view of the tissue retractor 100 showing the central body 102, the posterior housing 104, the right arm 106, the left arm 108 and the posterior arm 110. In this view both the central body 102 and the posterior housing 104 are in outline to show more details of the tissue retractor 100 and two way overrunning clutch 120, 130, 150 and 170 and how they are connected to the components. To extend or retract the posterior housing 104 in relation to the central body 102, the first two way overrunning clutch 130 is rotated. To extend or retract the posterior arm 110 in relation to the posterior housing 104, the second two way overrunning clutch 120 is rotated. To rotate the right arm 106 in relation to the central body 102, the third two way overrunning clutch 150 is rotated. To rotate the left arm 108 in relation to the central body 102, the fourth two way overrunning clutch 170 is rotated.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A tissue retractor comprising:
   a central body, a posterior housing, a posterior arm, a right arm and a left arm;
   a first two way overrunning clutch configured to extend or retract the posterior housing in relation to the central body;
   a second two way overrunning clutch configured to extend or retract the posterior arm in relation to the posterior housing;
   a third two way overrunning clutch configured to extend or retract the right arm in relation to the central body; and
   a fourth two way overrunning clutch configured to extend or retract the left arm in relation to the central body;
   wherein the first, second, third and fourth two way overrunning clutches are independently operated.

2. The tissue retractor of claim 1, wherein the posterior housing is slidably coupled to the central body.

3. The tissue retractor of claim 1, wherein the posterior arm is slidably coupled to the central body.

4. The tissue retractor of claim 1, wherein the right arm is rotatably coupled to the central body.

5. The tissue retractor of claim 1, wherein the left arm is rotatably coupled to the central body.

6. The tissue retractor of claim 1, wherein each of the first, second, third and fourth two way overrunning clutch include a top drive component and a bottom drive component, the top drive component being configured to couple with a tool to operate the two way overrunning clutch and the bottom drive component having a clutch gear configured to interface with gear teeth.

7. The tissue retractor of claim 6, wherein the first two way overrunning clutch is configured to fit within a first opening on the posterior housing and the first clutch gear is configured to mate with gear teeth in a first slot in the central body.

8. The tissue retractor of claim 6, wherein the second two way overrunning clutch is configured to fit within a second opening on the posterior housing and the second clutch gear is configured to mate with gear teeth in a second slot in the posterior arm.

9. The tissue retractor of claim 6, wherein the third two way overrunning clutch is configured to fit within a third opening on the central body and the third clutch gear of is configured to mate with gear teeth in a third slot in the right arm.

10. The tissue retractor of claim 6, wherein the fourth two way overrunning clutch is configured to fit within a fourth opening on the central body and the fourth clutch gear is configured to mate with gear teeth in a fourth slot in the left arm.

11. The tissue retractor of claim 6, wherein each of the first, second, third and fourth two way overrunning clutches include multiple pairs of leading edge rollers and trailing edge rollers separated by springs, with each pair being separated from adjacent pairs by legs on the top drive component.

12. A tissue retractor comprising:
a posterior housing slidably coupled to a central body;
a posterior arm slidably coupled to the posterior housing;
a right arm rotatably coupled to the central body via a hinge pin at a proximal end;
a left arm rotatably coupled to the central body via a hinge pin at a proximal end;
a first two way overrunning clutch configured to extend or retract the central body in relation to the posterior housing;
a second two way overrunning clutch configured to extend or retract the posterior arm in relation to the posterior housing;
a third two way overrunning clutch, the third two way overrunning clutch being configured to rotate a distal end of the right arm in relation to the central body; and
a fourth two way overrunning clutch configured to rotate a distal end of the left arm in relation to the central body.

13. The tissue retractor of claim 12, wherein each of the first, second, third and fourth two way overrunning clutch include a top drive component and a bottom drive component, the top drive component being configured to couple with a tool to operate the two way overrunning clutch and the bottom drive component having a clutch gear configured to interface with gear teeth.

14. The tissue retractor of claim 13, wherein the first two way overrunning clutch includes a first clutch gear configured to fit within a first slot on the central body and mate with gear teeth in the first slot.

15. The tissue retractor of claim 13, wherein the second two way overrunning clutch includes a gear configured to fit within a second slot on the posterior arm and mate with gear teeth in the second slot.

16. The tissue retractor of claim 13, wherein the third two way overrunning clutch includes a gear configured to fit within a third slot on the right arm and mate with gear teeth in the third slot.

17. The tissue retractor of claim 13, wherein the fourth two way overrunning clutch includes a gear configured to fit within a fourth slot on the left arm and mate with gear teeth in the fourth slot.

18. The tissue retractor of claim 13, wherein each of the first, second, third and fourth two way overrunning clutches include multiple pairs of leading edge rollers and trailing edge rollers separated by springs, with each pair being separated from adjacent pairs by legs on the top drive component.

19. A tissue retractor comprising:
a posterior housing slidably coupled to a central body;
a posterior arm slidably coupled to the posterior housing;
a right arm rotatably coupled to the central body;
a left arm rotatably coupled to the central body;
a first two way overrunning clutch configured to fit within a first opening on the posterior housing, the first two way overrunning clutch having a first clutch gear configured to mate with gear teeth in a first slot in the central body to extend or retract the central body in relation to the posterior housing;
a second two way overrunning clutch configured to fit within a second opening on the posterior housing, the second two way overrunning clutch having a second clutch gear configured to mate with gear teeth in a second slot in the posterior arm to extend or retract the posterior arm in relation to the posterior housing;
a third two way overrunning clutch configured to fit within a third opening on the right arm, the third two way overrunning clutch having a third clutch gear configured to mate with gear teeth in a third slot in the right arm to extend or retract the right arm in relation to the central body; and
a fourth two way overrunning clutch configured to fit within a fourth opening on the left arm, the fourth two way overrunning clutch being configured to extend or retract the left arm in relation to the central body.

20. The tissue retractor of claim 19, wherein each of the first, second, third and fourth two way overrunning clutches include multiple pairs of leading edge rollers and trailing edge rollers separated by springs, with each pair being separated from adjacent pairs by legs on the top drive component.

* * * * *